April 18, 1961 H. R. SCHENKEL, SR Plant Pat. 2,046
ROSE PLANT
Filed June 28, 1960
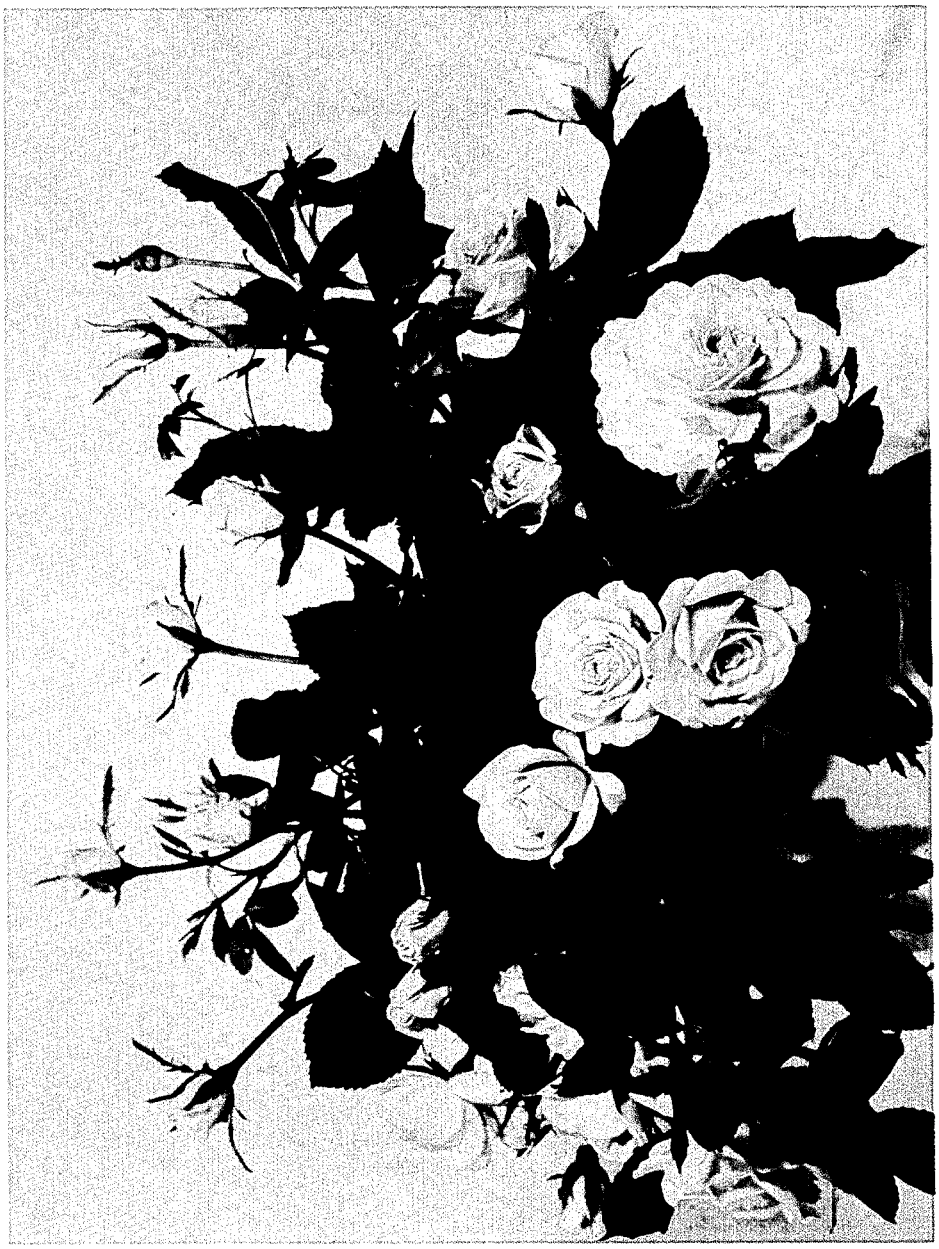
INVENTOR
H. R. Schenkel, Sr.
BY Robb & Robb
ATTORNEYS United States Patent Office Plant Pat. 2,046
Patented Apr. 18, 1961

2,046

ROSE PLANT

Herman R. Schenkel, Sr., Lynchburg, Va., assignor to H. R. Schenkel, Inc., Lynchburg, Va., a corporation of Virginia Filed June 28, 1960, Ser. No. 39,420

1 Claim. (Cl. 47—61)

The present invetnion relates to a new and distinct variety of rose plant of the floribunda class, which was discovered by me as a sport of the variety "Rosemary" (Plant Patent No. 1,398).

This new sport was discovered by me in one of the greenhouses of my assignee, located at Lynchburg, Virginia, while engaged in cutting flowers from bench plants of the variety "Rosemary" which were being grown under my direction and control. At the time I discovered the sport, my attention was attracted thereto by the distinctive form and clear color of the buds on one plant amongst the bench plants of "Rosemary." Upon closer examination of this plant, I found that it had sported and I thereupon took steps to carefully preserve the sport, keep it under observation, and to later asexually reproduce the same. These observations and asexual reproductions, the latter being made by me by top budding on greenhouse bench plants at Lynchburg, Virginia, as well as by top budding on *manetti* (a species botanically identified as *R. manetti* and widely used in the nursery industry as understock for commercially propagating rose plants), as performed on my behalf at Livermore, California, conclusively established important differences between the new sport and the parent variety "Rosemary," and that these different characteristics were fixed and established, and capable of being transmitted through succeeding propagations.

My new sport is generally similar to the parent variety "Rosemary," but is definitely distinguished therefrom, as well as from all other varieties of which I am aware, by the following characteristics which represent a new combination, particularly in the floribunda rose class:

(1) Somewhat narrower foliage and a distinctive color of the young foliage;

(2) A longer and more tapered form of the buds;

(3) Fewer flower petals;

(4) An unusual cleanliness and clarity of the flower color and the complete absence of green guard petals; and (5) A distinctive Rose Pink, lightly overcast with Deep Rose Pink general color tonality of the open flowers.

The accompanying drawing shows typical specimens of the vegetative growth and flowers of the new variety in different stages of development and as depicted in color as nearly true as it is reasonably possible to make the same in a color illustration of this character.

The following is a detailed description of my new rose variety, with color terminology in accordance with Ridgway's Color Standards and Nomenclature, as based upon specimens grown in a greenhouse at Lynchburg, Virginia:

Parentage: Sport of "Rosemary."

Classification:

*Botanic.*—Floribunda.

*Commercial.*—Floribunda.

Propagation: Holds its distinguishing characteristics through succeeding proagations by budding.

*Flower*

Blooming habit: Recurrent—continuous.

Bud:

*Size.*—Medium.

*Form.*—Ovoid; is not affected by wet or hot weather.

*Color.*—When sepals first divide—Cameo Pink, Plate 26. When petals begin to unfurl—Rosolane Pink, Plate 26, lightly overcast with Deep Rose Pink, Plate 12. When half-blown: inside of petals—Thulite Pink, Plate 26, lightly overcast with Deep Rose Pink, Plate 12; reverse of petals—Rosolane Pink, Plate 26, lightly overcast with Rose Pink, Plate 12 on the outer edge of the petals.

*Sepals.*—Branched; curl back when petals begin to unfurl. Color: inside—Deep Lichen Green, Plate 32; outside—Light Bice Green, Plate 17.

*Calyx.*—Color—Light Cress Green, Plate 31. Shape — pear. Size — small. Aspect — smooth. Odor when rubbed—none.

*Peduncle.* — Length — short. Aspect — rough. Strength — erect; slender. Color — Oil Green, Plate 5.

*Opening.*—Opens up well; is not affected by adverse weather conditions.

Bloom:

*Size.*—Medium. Average size when fully expanded—2 inches.

*Borne.*—Several together and in flat clusters.

*Stems.*—Medium length; normal strength.

*Form (when first open).*—Flat. Permanence—retains its form to the end.

*Petalage.*—Double (full but open center). Number of petals under normal conditions—from 45 to 50.

*Color.*—Center of flower—Deep Rose Pink, Plate 12. Outer petals—Rose Pink, Plate 12. Base of petals (aiglet)—Pale Turtle Green, Plate 32. Inside of petals—Rose Pink, Plate 12, lightly overcast with Deep Rose Pink, Plate 12. Reverse of petals—Cameo Pink, Plate 26, with upper half of petals overcast with Pale Amaranth Pink, Plate 12.

*Discoloration.*—General tonality at end of first day—Deep Rose Pink, Plate 12. Second day—Rose Pink, Plate 12, lightly overcast with Deep Rose Pink, Plate 12. Third day—Rose Pink, Plate 12.

Petals:

*Texture.*—Leathery; is not affected by wet or hot weather.

*Appearance.*—Inside—satiny. Outside—shiny.

*Form.*—Oval.

*Arrangement.* — Imbricated (regularly arranged shingle-like).

*Petaloids in center.*—Few; small.

*Persistence.*—Drop off cleanly.

*Fragrance.*—Moderate. Nature—tea (average hybrid tea scent).

*Lasting quality.*—On the plant—very long. As cut flower—very long.

*Genital organs*

Stamens, anthers: Small; many; regularly arranged around styles. Color—Light Orange-Yellow, Plate 3.

Stamens, filaments (threads): Short. Color—Pale Turtle Green, Plate 32.

Pollen: Color—Pale Orange-Yellow, Plate 3.

Styles: Bunched; uneven length; short; thin.

Stigmas: Color—Chartreuse Yellow, Plate 31.

Ovaries: All enclosed in calyx.

Hips: None.

Seeds: None.

*Plant*

Form: Bush.

Growth: Vigorous; branching (very free branching in greenhouse).

Foliage: Compound of 5 to 7 leaflets.

*Size.*—Medium.

*Quantity.*—Abundant.

*Color.*—New foliage: upper side—Hay's Maroon, Plate 13; under side—Mineral Red, Plate 27. Old foliage: upper side—Varley's Green, Plate 18; under side—Bice Green, Plate 17.

*Shape.*—Oval.

*Texture.* — Upper side — leathery. Under side—smooth.

*Ribs and veins.*—Ordinary.

*Edge.*—Serrated (saw-toothed).

*Serration.*—Both double and single; small.

*Leaf stem.*—Color—Biscay Green, Plate 27. Under side—prickly.

*Stipules.*—Medium length; bearded.

Wood:

*New wood.*—Color—Biscay Green, Plate 17. Bark—smooth.

*Old wood.* — Color — Light Elm Green, Plate 17. Bark—smooth.

Thorns:

*Thorns.*—Quantity: on main stalks from base—ordinary; on laterals from stalk—ordinary. Form—narrow base; medium length; hooked downward. Color (when young)—Carmine, Plate 1. Position—irregular.

*Prickles.*—Quantity: on main stalks—none; on laterals—none.

*Short needles.*—Quantity: on main stalks—none; on laterals—none.

I claim:

A new and distinct variety of rose plant of the floribunda class, substantially as herein shown and described, characterized particularly as to novelty by its general similarity to its parent variety "Rosemary" (Plant Patent No. 1,398), but being distinguished therefrom by the unique combination of somewhat narrower foliage and distinctive color of the young foliage, a longer and more tapered form of the buds, fewer flower petals, an unusual cleanliness and clarity of the flower color and complete absence of green guard petals, and a distinctive Rose Pink, lightly overcast with Deep Rose Pink general color tonality of the open flowers.

No references cited.